United States Patent
Borish et al.

(10) Patent No.: US 11,491,094 B2
(45) Date of Patent: *Nov. 8, 2022

(54) SULFATE-FREE SURFACTANT SYSTEM

(71) Applicant: Ethox Chemicals, LLC, Greenville, SC (US)

(72) Inventors: Edward T. Borish, Greenville, SC (US); Stephanie Anderson, Greenville, SC (US)

(73) Assignee: Ethox Chemicals, LLC, Greenville, SC (US)

( * ) Notice: Subject to any disclaimer, the term of this patent is extended or adjusted under 35 U.S.C. 154(b) by 203 days.

This patent is subject to a terminal disclaimer.

(21) Appl. No.: 17/072,318

(22) Filed: Oct. 16, 2020

(65) Prior Publication Data

US 2021/0113443 A1 Apr. 22, 2021

Related U.S. Application Data

(60) Provisional application No. 62/923,227, filed on Oct. 18, 2019.

(51) Int. Cl.
| | | |
|---|---|---|
| *A61K 8/37* | (2006.01) | |
| *A61K 8/34* | (2006.01) | |
| *A61K 8/41* | (2006.01) | |
| *A61K 8/03* | (2006.01) | |

(52) U.S. Cl.
CPC ............... *A61K 8/375* (2013.01); *A61K 8/03* (2013.01); *A61K 8/345* (2013.01); *A61K 8/41* (2013.01); *A61K 2800/10* (2013.01); *A61K 2800/30* (2013.01); *A61K 2800/48* (2013.01); *A61K 2800/596* (2013.01)

(58) Field of Classification Search
CPC .......... A61K 8/375; A61K 8/03; A61K 8/345; A61K 8/41; A61K 2800/10; A61K 2800/30; A61K 2800/48; A61K 2800/596; A61K 8/463; A61K 8/604; A61Q 19/00
See application file for complete search history.

(56) References Cited

U.S. PATENT DOCUMENTS

| | | |
|---|---|---|
| 9,090,727 B2 | 7/2015 | Hough et al. |
| 9,320,697 B2 | 4/2016 | Kleinen et al. |
| 9,579,272 B2 | 2/2017 | Galleguillos et al. |
| 9,931,290 B2 * | 4/2018 | Tamareselvy ............ A61Q 5/12 |
| 2009/0257968 A1 | 10/2009 | Walton et al. |
| 2011/0305648 A1 | 12/2011 | Knapek et al. |
| 2016/0279050 A1 | 9/2016 | Lu et al. |
| 2018/0071185 A1 | 3/2018 | Cochran et al. |
| 2020/0085713 A1 | 3/2020 | Gu et al. |

OTHER PUBLICATIONS

IPEA/US; Written Opinion of the International Preliminary Examining Authority; PCT/US2020/055934; Applicant: Ethox Chemicals, LLC; dated Oct. 27, 2021.
ISA/US; International Search Report and Written Opinion; PCT/US2020/055934; Applicant: Ethox Chemicals, LLC; dated Mar. 8, 2021.

* cited by examiner

*Primary Examiner* — Isaac Shomer
*Assistant Examiner* — Amanda Michelle Petritsch
(74) *Attorney, Agent, or Firm* — Joseph T. Guy; Patent Filing Specialist Inc.

(57) ABSTRACT

Provided is a sulfate-free surfactant system which is particularly suitable for use in personal hygiene products. The sulfate-free surfactant system comprises a liquid comprising an organic phase and a solvent wherein the organic phase comprises glyceride and surfactant and the liquid comprises: 4-40 wt % glyceride wherein the glyceride is the condensation reaction product of at least 1.10 moles of a mixture of acids to no more than 2.1 moles of mixture of acids per mole of glycerin;
wherein mixture of acids comprises:
at least 0.275 to no more than 0.990 moles of a first acid comprising a branched acid with 16-20 aliphatic carbons;
at least 0.250 to no more than 0.810 moles of a second acid comprising an alkyl acid with 9-11 carbons; and
at least 0.250 to no more than 0.810 moles of a third acid comprising an alkyl acid with 7-9 carbons wherein the third acid has a lower molecular weight than the second acid; and
6-45 wt % surfactant; and
wherein the liquid has a BYV of at least 50 dyn/cm$^2$.

54 Claims, No Drawings

SULFATE-FREE SURFACTANT SYSTEM

CROSS-REFERENCE TO RELATED APPLICATIONS

The present invention claims priority to pending U.S. Provisional Patent Application No. 62/923,227 filed Oct. 18, 2020 which is incorporated herein by reference.

FIELD OF THE INVENTION

The present invention is related to an improved surfactant system which is particularly suitable for use in sulfate-free liquid compositions as used in personal hygiene products and the like. More specifically, the present invention is related to an improved system for thickening a sulfate-free liquid surfactant composition.

BACKGROUND

There is an on-going need for improved personal hygiene and personal treatment compositions. A particular aspect of this on-going desire is the use of sulfate-free formulations. Sulfate-based surfactants are known to be an irritant to mucosal membranes and particularly those membranes associated with the eyes, the skin and the lungs. It has therefore been a societal desire to remove sulfate-based surfactants from personal hygiene products, particularly liquid products, including but not limited to those used for cleansing hair and skin.

Unfortunately, consumers have developed an expectation in personal hygiene products which has limited the growth of sulfate-free personal hygiene products. Of particular importance to consumers is viscosity. It is desirable that personal hygiene products have a viscosity that makes the product easy to control during application and which does not flow to unintended areas of the body. If the viscosity is too low the product spreads quickly and may run out of the consumers hand during application or run down the consumers face or down the nape of the neck, in the case of shampoo for example, which is undesirable.

With sulfate-based surfactants, and non-aqueous solvent based systems, viscosity is easily controlled by salts. In these systems the viscosity generally increases with concentration of salt, within the working range, even up to a viscosity sufficient to form a solid, non-flowable gel. As set forth in U.S. Published Patent Application No. 2009/0257968, particularly suitable salts for increasing viscosity contain cations such as alkali metals, particularly sodium and potassium; and alkali metal salts, such as magnesium and aluminum. However, salts are not effective in controlling the viscosity of non-sulfate aqueous based systems. This has led to efforts to develop a surfactant system suitable for controlling the viscosity of sulfate-free liquid compositions. Presented herein is a sulfate-free surfactant system suitable for use in aqueous liquid compositions which is particularly desirable for use in personal hygiene products and the like without limit thereto.

With sulfate-free surfactant systems comprising amphoteric, anionic, nonionic or cationic surfactants in aqueous solutions it is challenging to find a naturally derived viscosity modifier that also provides desired rheology properties. These products are typically used, but not confined to, the personal care market in the form of shampoos, body washes, and liquid hand soaps as well as in household products such as dishwashing detergents. Natural gums can be used however, they are difficult to use and have poor aesthetics.

The present invention provides a natural based thickener which is particularly suitable for use in sulfate-free liquid surfactant systems which is suitable for use in personal hygiene products, and the like, and which provides a composition with non-Newtonian rheology.

SUMMARY OF THE INVENTION

The present invention is related to a sulfate-free liquid surfactant system.

More specifically, the present invention is related to a sulfate-free liquid surfactant system comprising a thickener which can provide a non-Newtonian liquid with shear thinning properties.

A particular feature of the invention is a thickener, based on natural products, which can be used in a sulfate-free liquid surfactant system which is biologically compatible and safe.

These and other embodiments, as will be realized, are provided in a sulfate-free surfactant system comprising:
a liquid comprising an organic phase and a solvent wherein the organic phase comprises glyceride and surfactant and the liquid comprises:
4-40 wt % glyceride wherein the glyceride is the condensation reaction product of at least 1.10 moles of a mixture of acids to no more than 2.1 moles of mixture of acids per mole of glycerin;
wherein mixture of acids comprises:
at least 0.275 to no more than 0.990 moles of a first acid comprising a branched acid with 16-20 aliphatic carbons;
at least 0.250 to no more than 0.810 moles of a second acid comprising an alkyl acid with 9-11 carbons; and
at least 0.250 to no more than 0.810 moles of a third acid comprising an alkyl acid with 7-9 carbons wherein the third acid has a lower molecular weight than the second acid; and
6-45 wt % surfactant; and
wherein the liquid has a BYV of at least 50 dyn/cm$^2$.

Yet another embodiment is provided in a method of forming a sulfate-free surfactant system comprising:
forming an organic phase comprising:
forming a glyceride by reacting a mixture of acids with glycerin wherein the mixture of acids comprises 1.1 to 2.1 moles of acid per mole of glycerin; and
mixing the glyceride with a surfactant selected from group consisting of a cationic surfactant, a anionic surfactant, a nonionic surfactant and an amphoteric surfactant or mixtures thereof.

Yet another embodiment is provided in a personal hygiene product comprising a sulfate-free surfactant system comprising:
a liquid comprising an organic phase and a solvent wherein the organic phase comprises glyceride and surfactant and liquid comprises:
4-40 wt % glyceride wherein the glyceride is the condensation reaction product of at least 1.10 moles of a mixture of acids to no more than 2.1 moles of mixture of acids per mole of glycerin;
wherein the mixture of acids comprises:
at least 0.275 to no more than 0.990 moles of a first acid comprising a branched acid with 16-20 aliphatic carbons;
at least 0.250 to no more than 0.810 moles of a second acid comprising an alkyl acid with 9-11 carbons; and at least 0.250 to no more than 0.810 moles of a third acid comprising an alkyl acid with 7-9 carbons wherein the third acid has a lower molecular weight than the second acid; and 6-45 wt % surfactant; and wherein the liquid has a BYV of at least 50 dyn/cm$^2$.

DESCRIPTION

The present invention is related to a sulfate-free liquid surfactant system which is particularly suitable for use in personal hygiene products. More specifically, the present invention is related to a natural based glyceride or glyceryl ester which is particularly suitable as a thickener for sulfate-free liquid surfactant systems which are non-Newtonian liquids.

The glyceride is formed as the reaction product of glycerin with a molar excess of a mixture of acids. The molar excess provides, on average, primarily mono and diglyceride esters. More specifically, the molar excess is at least a 10% molar excess to no more than 110% molar excess. Even more specifically, for one mole of glycerin at least 1.10 moles of the mixture of acids is used to no more than 2.10 moles of the mixture of acids. Below about 1.10 moles of the mixture of acids per mole of glycerin the number of diglyceride esters, based on statistical distribution, is insufficient for the surfactant to provide sufficient thickening efficiency at reasonable concentrations. Above about 2.10 moles of the mixture of acids per mole of glycerin the number of triglyceride esters, based on statistical distribution, increases and is no longer a surfactant suitable for the intended purpose.

The mixture of acids comprises three acids with the first acid having a higher molecular weight than the second acid wherein the second acid has a higher molecular weight than the third acid. The first acid is preferably a branched acid comprising 16-20 aliphatic carbons and preferably 18 aliphatic carbons. Particularly preferred as the first acid is a methyl branched aliphatic carbon with 16-methylheptadecanoic acid being particularly preferred. The second acid is preferably an alkyl acid of 9-11 carbons which are preferably unbranched and more preferably the second acid is decanoic acid. The third acid is preferably an alkyl acid of 7-9 carbons which are preferably unbranched and more preferably the third acid is octanoic acid.

The mixture of acids comprises, per mole of glycerin, at least 0.275 to no more than 0.990 moles of the first acid; at least 0.250 to no more than 0.810 moles of the second acid and at least 0.250 to no more than 0.810 moles of the third acid. More preferably, the mixture of acids comprises, per mole of glycerin, at least 0.425 moles of the second acid, even more preferably at least 0.520 moles of the second acid, even more preferably no more than 0.580 moles of the second acid. More preferably, the mixture of acids comprises, per mole of glycerin, at least 0.425 moles of the third acid, even more preferably at least 0.520 moles of the third acid, even more preferably no more than 0.580 moles of the third acid.

The sulfate-free surfactant system preferably comprises an organic phase comprising at least 4 wt % glyceride to no more than 50 wt % glyceride ester and at least 6 wt % surfactant to no more than 45 wt % surfactant with the balance being water and other excipients. Below about 4 wt % glyceride the thickening properties are insufficient and above about 50 wt % glyceride insufficient additional benefits are observed to justify the further addition.

The sulfate-free surfactant system preferably comprises at least 10 wt % to no more than 95 wt % organic phase and 5 wt % to no more than 90 wt % water. Other additives commonly employed in personal hygiene products can be employed including, without limit thereto, fragrances, colorants, chelating agents, abrasives, anti-deposition agents, brightening agents, UV-absorbers, preservatives, antioxidants, sunscreen agents, vitamins, dyes, hair coloring agents, proteins, amino acids, natural extracts such as plant extracts, humectants, perfumes, oils, emollients, lubricants, butters, penetrants, thickeners, viscosity modifiers, polymers, resins, hair fixatives, film formers, surfactants, detergents, emulsifiers, opacifying agents, volatiles, propellants, liquid vehicles, carriers, salts, pH adjusting agents (e.g., citric acid), neutralizing agents, buffers, hair conditioning agents, anti-static agents, antifrizz agents, anti-dandruff agents, absorbents, and combinations thereof.

A particularly preferred embodiment comprises a mixture of: 10-30 wt % glyceride; 20-40 wt % sulfate-free surfactant system with disodium laureth sulfosuccinate, decyl glucoside sodium lauroyl lactylate, or sodium lauriminodipropionate and 30-70 wt % water. A particularly preferred glyceride comprises the reaction of glycerin with isostearic acid, octanoic acid and decanoic acid.

The reaction of the mixture of acids and glycerin provides a statistical mixture of esters with each ester being the product of a condensation reaction between one randomly selected hydroxyl group on a glycerin molecule and one of either the first acid, second acid or third acid. It is assumed that all acid molecules react and therefore the average number of esters formed per glycerin molecule is approximately the molar ratio of mixed acid to glycerin, which is 1.1 to 2.1. By way of non-limiting example if 1.5 moles of mixed acid is reacted with 1 mole of glycerin the average number of esters per glycerin molecule is defined as 1.5.

The glyceride provides viscosity and the desired shear thinning rheology properties without sacrificing foam properties of the surfactant. It also adds lubricity and emolliency to the finished product thereby allowing the formulator to reduce additional ingredients to achieve preferred aesthetics in the finished product.

The glyceride is formed by heating glycerin and the prescribed mixture of acids under nitrogen with mixing, preferably to an initial temperature of 160° C. Then the temperature increased 10° C. every hour until reaching 220° C. Samples are taken every 4 hours until the reaction is complete, followed by cooling to 40-50° C. and filtering.

The sulfate-free liquid surfactant system can be made either by mixing the surfactants with the glyceride followed by the addition of the mixture to the water, addition of water to the mixture or all components can be added at the same time, heated and stirred preferably for about 10 minutes.

A particular feature of the claimed invention is the surprising and unexpected ability to provide a non-Newtonian liquid with shear-thinning properties which provides a satisfactory feel when used by consumers. A liquid that has a lower viscosity under high shear than under low shear has shear-thinning rheology. When used in personal hygiene products this provides many benefits. The liquid can be dispensed through an orifice, since the viscosity lowers under the higher shear stress of the orifice. However, the viscosity increases once dispensed and therefore the liquid can be applied with minimal flow. Furthermore, the non-Newtonian liquid will suspend bubbles or particulate therein during storage thereby reducing the settling that occurs in the absence of this type of Rheology.

Shear-thinning is quantified by the Brookfield Yield Value (BYV) which is calculated by the equation:

$$BYV = 2r_1(n_1 - n_2)/100$$

wherein $n_1$ and $n_2$ are the viscosities at two different spindle speeds, $r_1$ and $r_2$, wherein $r_2/r_1=2$. BYV is reported as dyn/cm². For the purposes of this invention BYV is measured at ambient temperature, about 25° C. Viscosities were determined at spindle speeds of 10 and 20 rpm using a Brookfield DV-II+ Viscometer and reported as centipoise (cps). A positive BYV indicates shear-thinning. For the purposes of the present invention a BYV of at least 50 dyn/cm² is preferred. It is more preferable that the shear-thinning be at least 100 dyn/cm². Above a BYV of about 100 dyn/cm² the liquid can suspend particles with an average particle diameter of 0.6 mm such as sand. It is preferable that the BYV no exceed 100,000 dyn/cm².

In some instances the liquid may also be rheopectic as evidenced by a time-dependent shear thickening.

A particularly preferred surfactant system comprises the glyceride and at least one surfactant which is defined as a compound which lowers the surface tension of a liquid. Preferred surfactants are selected from an anionic surfactant, a cationic surfactant, a nonionic surfactant and an amphoteric surfactant.

Preferred anionic surfactants include glutamates, taurates, alkanoyl isethionates, alkyl succinates, alkyl sulphosuccinates, N-alkoyl sarcosinates, alkyl phosphates, alkyl ether phosphates, alkyl ether carboxylates, alpha-olefin sulphonates wherein alkyl and acyl groups are preferably 8 to 18 carbons which may be unsaturated. Particularly preferred alpha-olefin sulphonates include the sodium, magnesium, ammonium and mono-, di- and triethanolamine salts thereof. Particularly preferred anionic surfactants include sodium oleyl succinate, ammonium lauryl sulphosuccinate, disodium laureth sulfosuccinate, sodium dodecylbenzene sulphonate, triethanolamine dodecylbenzene sulphonate, sodium cocoyl isethionate, sodium lauroyl isethionate, sodium N-lauryl sarconsinate, sodium lauroyl lactylate, sodium lauroyl glutamate, sodium methyl cocoyl taurate, sodium lauroyl methyl taurate, sodium lauriminodipropionate and mixtures thereof.

Particularly preferred cationic surfactants include quaternized amines, quaternized polysaccharides, alkyl polysaccharides, alkoxylated amines, alkoxylated ether amines, phospholipids, phospholipid derivatives, and mixtures thereof.

Preferred nonionic surfactants include polyalkylene glycol adducts of alcohols, acids & glycerides, polyglycerin adducts of acids & alcohols, alkyl glucosides, sorbitan esters, fatty acid amides, and polyoxyethylene, polyoxypropylene block copolymers, in particular, the following surfactants, alone or as mixtures. Particularly preferred nonionic surfactants include polyalkylene glycol adducts of alkyl C8-C24 phenols; polyalkylene glycol adducts of C8-C30 alcohols or C8-C30 glycosides, linear or branched, saturated or unsaturated; polyalkylene glycol adducts of C8-C30, linear or branched, saturated or unsaturated fatty acid amides; C8-C30 linear or branched, saturated or unsaturated esters of sorbitol, which are preferably polyalkylene glycol adducts; fatty acid esters of sucrose; C8-C30 alkyl polyglycosides; C8-C30 alkenyl polyglycosides, which are optionally polyalkylene glycol adducts with from 0 to 10 polyalkylene glycol units and comprising from 1 to 15 glucose units; polyalkylene glycol adducts of saturated or unsaturated vegetable oils; derivatives of N-alkyl (C8-C30) glucamine; derivatives of N-acyl C8-C30 methylglucamine; aldobionamides; amine oxides; polyalkylene glycol adducts of silicones; polyglycerin adducts of lauryl alcohol containing 1-7 moles of glycerin; polyglycerin adducts of oleyl alcohol containing 1-7 moles of glycerin; polyglycerin adducts of cetearyl alcohol containing 1-7 moles of glycerin; polyglycerin adducts of octadecanol containing 1-7 moles of glycerin and alkyl glucosides including without limitation decyl glucoside, lauryl glucoside, coco glucoside, and caprylic/capric glucoside.

Throughout the specification the term "Cx" refers to x carbons. By way of non-limiting example, C8 refers to a specified group with eight carbons.

Particularly preferred amphoteric surfactants include cocamidopropyl hydroxysultaine, cocamidopropyl betaine and cocobetaine, the sodium salt of diethylaminopropyl laurylaminosuccinamate or mixtures thereof.

The present invention is suitable for use in any application desiring thickening of a sulfate-free surfactant system. The present invention is particularly suitable for personal hygiene products but is also suitable without limitation for use for cleaning surfaces including metal surfaces, porous surfaces, ceramic surfaces, smooth surfaces, painted surfaces, and natural surfaces such as cellulose based materials.

For the purposes of the present invention personal hygiene products refer to those products which are intended for use to cleanse, purify, or otherwise treat primarily the skin, hair or nails of the consumer without limit thereto. Particularly suitable personal hygiene products for demonstration of the invention include, without limit thereto, a shampoo, a conditioner, a hand wash, a face wash, a body wash, a hand soothing liquid, an aromatic liquid, an eye care product, a cosmetic, a fragrance, a hair coloring formulation, a hair straightening or permanent wave formulation, a nail care formulation, a toothpaste, a mouthwash, a shave cream, a skin care formulation, a sun care formulation, a lip care formulation, an antiperspirant, or a foot care formulation.

For the purposes of the present invention the term "sulfate-free" refers to a surfactant system comprising less than 2 wt % sulfate-based surfactant, preferably less than 1 wt % sulfate-based surfactant and most preferably less than a measurable amount of sulfate-based surfactant. A sulfate-based surfactant is one characterized by the following chemical structure:

$$R\text{—}OSO_3^{-1}$$

where R is a lipophilic group.

Listed ranges for composition are inclusive and include every number with the same number of significant figures in the range. By way of non-limiting example, a stated range of 0.001 to 0.010 would include 0.001, 0.002, 0.003, 0.004, 0.005, 0.006, 0.007, 0.008, 0.009 and 0.010.

EXAMPLES

Preparation of Esters

Ester 1 would be prepared by reacting 1 mole of glycerin (99.7%) with 2 moles of a mixture of acids where the acid mix comprises 25 wt % isostearic acid and 34 wt % octanoic acid and 41 wt % decanoic acid. The mixture would be made as described above.

Ester 2 would be prepared by the same procedure as Ester 1 using slightly more than 1 mole of a mixture of acids where the acid mix is 36 wt % isostearic acid and 32wt % octanoic acid and 32 wt % decanoic acid.

Ester 3 would be prepared by the same procedure as Ester 2 with 26 wt % isostearic acid, 22 wt % caprylic acid and 22 wt % decanoic acid per mole of glycerin.

Preparation of Mixtures

Example 1

50 grams of sodium laurimidopropyldipropionate (DeTERIC LP from Deforest Surfactants as 30% active) was mixed with 20 grams of Ester 3 and heated at 38° C. for 10 minutes. The mixture was then cooled to room temperature resulting in a thick cream.

Example 2

40 grams of laurimidopropyldipropionate (DeTERIC LP from Deforest Surfactants as 30% active) was mixed with 10 grams of Ester 3 at room temperature resulting in a thickened mixture.

Example 3

50 grams of laurimidopropyldipropionate (DeTERIC LP from Deforest Surfactants as 30% active) was mixed with 10 grams of Ester 3 and heated at 38° C. for 10 minutes. The mixture was cool to room temperature resulting in little or no thickening.

Example 4

40.0 grams of laurimidopropyldipropionate (DeTERIC LP from Deforest Surfactants as 30% active) was mixed with 40.0 grams of Ester 3 and 10.0 grams of water. This mixture was not very thick even after heating.

Example 5

A mixture of 21.0 grams of Ester 3 and 83.0 grams of disodium laureth sulfosuccinate (Making Cosmetics, 32% active) was heat at 38° C. for 10 minutes. The mixture began to thicken after about 2 minutes.

Example 6

5.0 grams of the mixture from Example 5 was added to 45.0 grams of water followed by heating at 38° C. for 10 minutes resulting in a mixture with low viscosity.

Example 7

5.0 more grams of the mixture from Example 5 was added into the mixture of Example 6 followed by heating at 38° C. for 10 minutes resulted in a mixture with low viscosity.

Example 8

5.7 more grams of the mixture from Example 5 was added to the mixture of Example 7 followed by heating at 38° C. for 10 minutes resulting in a thickened mixture.

Example 9

20.0 grams of Ester 3 was mixed with 40.0 grams of disodium laureth sulfosuccinate (Making Cosmetics, 32% active) at room temperature. 40.0 grams of water was then added and the resultant mixture was mixed at 43° C. for 10 minutes. This mixture began to thicken after about 1 minute of heating.

Example 10

20.0 grams of Ester 3 was mixed with 67.0 grams of disodium laureth sulfosuccinate (Making Cosmetics, 32% active) at room temperature resulting in a thickened mixture.

Example 11

13.0 grams of water was added to the mixture from Example 10 at room temperature resulting in a viscous mixture having a Brookfield viscosity of 193,000 cps at 10 rpms and a 100,000 cps at 20 rpms. The mixture had a BYV of 18,600 dyn/cm$^2$.

Example 12

10.0 grams of Ester 3 were mixed with 20.0 grams of disodium laureth sulfosuccinate (Making Cosmetics, 32% active) at room temperature producing an opaque gel. The mixture was stirred at 50° C. for 5 minutes and then cooled to room temperature.

Example 13

30.0 grams of water was added to the mixture from Example 12 resulting in a gel.

Example 14

5.0 grams of Ester 3 was mixed with 20.0 grams of disodium laureth sulfosuccinate (Making Cosmetics, 32% active) at room temperature. The result was a thick mixture which would give stiff peaks.

Example 15

20.0 grams of water were added to the mixture of Example 14. The mixture became thin and failed to regain viscosity even after heating at 80° C. for 10 minutes.

Example 16

21.0 grams of Ester 3 were added to 83.0 grams of a blend of decyl glucoside and sodium lauroyl lactylate (Making Cosmetics, 54% active) followed by heating at 43° C. for 10 minutes. The mixture began to thicken after 2 minutes.

Example 17

50.0 grams of water were added to 50.0 grams of the mixture from Example 16 resulting in a thickened mixture having a suitable viscosity.

Example 18

20.0 grams of Ester 3 was added to 40.0 grams of a blend of decyl glucoside and sodium lauroyl lactylate (Making Cosmetics, 54% active) at room temperature resulting in a thickened mixture. The thickened mixture was then heated at 43° C. for ten minutes and then cooled to room temperature.

Example 19

40.0 grams of water were added to the mixture of Example 18 resulting in a thickened mixture having a Brookfield viscosity of 13,000 cps at 10 rpm and 8,000 at 20 rpm. The BYV was 1,000 dyn/cm$^2$. This sample also demonstrated rheopectic or time-dependent shear-thickening rheology.

Example 20

20.0 grams of Ester 3 was added to 67.0 grams of Endinol Mild B 65 SF Blend (Coast Southwest, 30% active) at room temperature resulting in a thickened mixture. Endinol Mild B 65 SF Blend is a commercially available blend of sodium cocoyl isethionate, cocamido hydroxysultaine, lauryl glucoside, cocamidopropylamine oxide and caprylyl/capryl glucoside.

Example 21

30 grams of water was added to the mixture of Example 20 resulting in a thickened mixture.

Example 22

10.0 grams of Ester 3 were added to 21.0 grams of Endinol Mild B 65 SF Blend (Coast Southwest, 30% active) at room temperature resulting in a thickened white mixture. The mixture was heated at 50° C. for 10 minutes and then cooled to RT.

Example 23

30.0 grams of water was added to the mixture of Example 22 resulting in a thick conditioner-like consistency that formed soft peaks.

Example 24

10.0 grams of Ester 3 were added to 20.0 grams of cocamidopropyl hydroxysultaine (Sopalteric CHS from Coast Southwest, 50% active) at room temperature resulting in a thick white mixture which was heated for ten minutes at 50° C. and then cooled to room temperature.

Example 25

30.0 grams of water was added to the mixture of Example 24 resulting in a thick conditioner-like consistency that formed soft peaks.

Example 26

10 grams of Ester 3 were mixed with 20 grams of cocamidopropyl betaine (Enditeric COAB from Coast Southwest, 30% active) resulting in a thick white mixture. The mixture was heated for 10 minutes at about 50° C. and then cooled to room temperature.

Example 27

30 grams of water were added to the mixture of Example 26 resulting in a thickened mixture.

Example 28

2.5 grams of sodium cocoyl isethionate (Aminosyl SCI from JARCHEM, 86% active) was mixed with 17.5 grams of water and heated until clear at about 60° C. 5 grams of Ester 3 was mixed in resulting in a thick opaque mixture. This mixture was heated at about 60-70° C. for about 5 minutes resulting in a very thick cream. The mixture had a Brookfield Viscosity of 84,000 cps at 10 rpm and 44,000 cps at 20 rpm. The BYV was 8,000 dyn/cm$^2$.

Example 29

5.0 grams of sodium cocoyl isethionate (Aminosyl SCI from JARCHEM, 86% active) was added to 10.0 grams of water and heated until clear at about 80-90° C. 10 grams of Ester 3 was then mixed in resulting in a thick gel. The mixture had a Brookfield Viscosity of 78,000 cps at 10 rpm and 47,000 cps at 20 rpm. The BYV was 6,200 dyn/cm$^2$.

Example 30

20.0 grams of sodium lauroyl sarcosinate (Aminosyl L-30 from JARCHEM, 30% active) was added to 20 grams water at room temperature resulting in an opaque viscous gel. This mixture was heated at about 50° C. for about 10 minutes and then cooled to room temperature. The addition of heat seemed to cause further thickening. 20 grams of water was slowly added to the above mixture giving a very foamy/aerated somewhat viscous composition. After the addition of water the mixture was heated at about 60° C. for about 10 minutes, however no additional increase in viscosity was observed. The mixture had a Brookfield Viscosity of 1,400 cps at 10 rpm and 800 cps at 20 rpm. The BYV was 2,200 dyn/cm$^2$.

Example 31

2.5 grams of sodium lauroyl glutamate (Aminosyl SLG from JARCHEM, 94% active) was added to 17.5 grams of water and heated at 40-50° C. until clear. 5.0 grams of Ester 3 was added followed by heating at about 70-80° C. for 5 minutes resulting in a white viscous mixture. The mixture had a Brookfield Viscosity of 7,700 cps at 10 rpm and 4,500 cps at 20 rpm. The BYV was 620 dyn/cm$^2$.

Example 32

3.5 grams of sodium lauroyl glutamate (Aminosyl SLG from JARCHEM, 94% active) was added to 14.5 grams of water and heated at about 60-70° C. until clear. 7.0 grams of Ester 3 was added followed by heating at about 70-80° C. for 5 minutes resulting in a white viscous mixture. The mixture had a Brookfield Viscosity of 196,000 cps at 10 rpm and 114,000 cps at 20 rpm. The BYV was 16,400 dyn/cm$^2$.

Example 33

5.0 grams of sodium lauroyl glutamate (Aminosyl SLG from JARCHEM, 94% active) was added to 10.0 grams of water and heated at 40-50° C. until clear. 8.5 grams of Ester 3 was added resulting a very firm opaque gel. The mixture had a Brookfield Viscosity of 250,000 cps at 10 rpm and 147,000 cps at 20 rpm. The BYV was 20,600 dyn/cm$^2$.

Example 34

10.0 grams of sodium methyl cocoyl taurate (Aminosyl SMCT from JARCHEM, 25% active) was added to 20.0 grams of water and heated to about 70° C. until clear followed by the addition of 8 grams of Ester 3. The resultant mixture was heated at about 70° C. for 5 minutes. The mixture was cooled to room temperature resulted in a viscous white mixture. The mixture had a Brookfield Viscosity of 5,600 cps at 10 rpm and 3,400 cps at 20 rpm. The BYV was 440 dyn/cm$^2$.

Example 35

3.5 grams of sodium methyl cocoyl taurate (Aminosyl SMCT from JARCHEM, 25% active) was added to 14.5 grams of water and heat to about 35° C. until clear followed by cooling to room temperature. 3.5 grams of Ester 3 was added and the mixture heated and stirred at room temperature for 10 minutes resulting in a very viscous opaque, white mixture. The mixture had a Brookfield Viscosity of 2,000 cps at 10 rpm and 1,300 cps at 20 rpm. The BYV was 140 dyn/cm$^2$.

Example 36

2.5 grams of sodium methyl cocoyl taurate (Aminosyl SMCT from JARCHEM, 25% active) was added to 17.5 grams of water and heated to about 40-50° C. until clear. 5.0 grams of Ester 3 was added and the mixture was heated at 70° C. for 5 minutes. On cooling to room temperature the mixture separated.

Example 37

10.0 grams of sodium methyl cocoyl taurate (Aminosyl SMCT from JARCHEM, 25% active) was added to 20.0 grams of water and heated to about 50-60° C. until clear. 20.0 grams of Ester 3 was added at about 70° C. At about 7-8 grams of added Ester 3 the mixture was a thick gel even when hot. Further addition made the mixture thinner and on cooling to room temperature the mixture separated.

Example 38

3.5 grams of sodium methyl cocoyl taurate (Aminosyl SMCT from JARCHEM, 25% active) was added to 14.5 grams of water and heated to about 35° C. until clear followed by cooling to room temperature. 7 grams of Ester 3 was added to the cooled solution. At about 3-3.5 grams of added Ester 3 the mixture turned opaque and thickened. Further addition made the mixture thinner and clearer. Heating to 60-70° C. for 5 minutes caused no thickening. On cooling to room temperature the mixture separated.

Example 39

3.5 grams of sodium lauroyl methyl taurate (Aminosyl SLMT from JARCHEM, 97% active) was added to 14.4 grams of water and heated to about 70° C. with mixing till clear. 7 grams of Ester 3 was then added and the mixture cooled to room temperature. The mixture was extremely thick even at 70° C. The mixture had a Brookfield Viscosity of 135,000 cps at 10 rpm and 76,000 cps at 20 rpm. The BYV was 11,800 dyn/cm$^2$. The sample also demonstrated rheopectic or time-dependent shear-thickening rheology.

Example 40

3.5 grams of behentrimonium chloride and isopropyl alcohol (Incroquat TMC-85 from Croda, 85% active) was added to 14.5 grams of water and heated till clear at about 80-90° C. The mixture was cooled to about 60-70° C. and then 3 grams of Ester 3 was mixed in. This mixture very thick even while still hot. The mixture had a Brookfield Viscosity of 90,000 cps at 10 rpms and 55,000 cps at 20 rpms. The BYV was 7,000 dyn/cm$^2$. This sample was also rheopectic.

Example 41

7 grams of Ester 3 were added to 20 grams of decyl glucoside (Sucranov 2000UP from JARCHEM, 50% active) at room temperature. The mixture was heated to 50° C. followed by the addition of 3 more grams of Ester 3 followed by holding at 50° C. for 5 minutes. After cooling to room temperature 10 grams of water was added to the mixture. The mixture had a Brookfield Viscosity of 42,500 cps at 10 rpm and 28,500 cps at 20 rpm. The BYV was 280 dyn/cm$^2$.

Example 42

7 grams of Ester 3 were added to 20 grams of decyl glucoside (Sucranov 2000UP from JARCHEM, 50% active) at room temperature. This mixture was very thick. The mixture had a Brookfield Viscosity of 92,000 cps at 10 rpm and 46,000 cps at 20 rpm. The BYV was 920 dyn/cm$^2$.

Example 43

13 grams of water was added to the mixture of Example 42 at room temperature resulting in a viscous mixture. The mixture had a Brookfield Viscosity of 36,500 cps at 10 rpm and 20,000 cps at 20 rpm. The BYV was 330 dyn/cm$^2$.

Example 44

The sample of Example 43 was heated at 50-60° C. for 5 minutes resulting in a slight increase in viscosity.

Example 45

20 grams of decyl glucoside (Sucranov 2000UP from JARCHEM, 50% active) was neutralized using 50 wt % solution of citric acid in water to pH 5-6. To this was added 7 grams of Ester 3 with mixing at room temperature. This resultant mixture was very thick. 13 grams of water was added resulting in a viscous gel.

The Examples demonstrate that viscosity is dependent on the total amount of Ester 3 and surfactant as well as the ratio of Ester 3/surfactant and that heat is not necessarily required to build viscosity.

The invention has been described with reference to the preferred embodiments without limit thereto. Additional embodiments and improvements may be realized which are not specifically set forth herein but which are within the scope of the invention as more specifically set forth in the claims appended hereto.

The invention claimed is:
1. A sulfate-free surfactant system comprising:
  a liquid comprising an organic phase and a solvent wherein said organic phase comprises glyceride and surfactant and said liquid comprises:
  4-40 wt % glyceride wherein said glyceride is the condensation reaction product of at least 1.10 moles of a mixture of acids to no more than 2.1 moles of said mixture of acids per mole of glycerin;
  wherein said mixture of acids comprises:
  at least 0.275 to no more than 0.990 moles of a first acid comprising a branched acid with 16-20 aliphatic carbons;
  at least 0.250 to no more than 0.810 moles of a second acid comprising an alkyl acid with 9-11 carbons; and
  at least 0.250 to no more than 0.810 moles of a third acid comprising an alkyl acid with 7-9 carbons wherein said third acid has a lower molecular weight than said second acid; and
  6-45 wt % surfactant; and
  wherein said liquid has a BYV of at least 50 dyn/cm$^2$.
2. The sulfate-free surfactant system of claim 1 wherein said solvent is water.

3. The sulfate-free surfactant system of claim 2 comprising 10 to 95 wt % said organic phase and 10-90 wt % water.

4. The sulfate-free surfactant system of claim 1 wherein said BYV is at least 100 dyn/cm$^2$.

5. The sulfate-free surfactant system of claim 1 wherein said BYV does not exceed 100,000 dyn/cm$^2$.

6. The sulfate-free surfactant system of claim 1 wherein said mixture of acids comprises at least 0.425 moles of said second acid.

7. The sulfate-free surfactant system of claim 6 wherein said mixture of acids comprises at least 0.520 moles of said second acid.

8. The sulfate-free surfactant system of claim 1 wherein said mixture of acids comprises no more than 0.580 moles of said second acid.

9. The sulfate-free surfactant system of claim 1 wherein said mixture of acids comprises at least 0.425 moles of said third acid.

10. The sulfate-free surfactant system of claim 9 wherein said mixture of acids comprises at least 0.520 moles of said third acid.

11. The sulfate-free surfactant system of claim 1 wherein said mixture of acids comprises no more than 0.580 moles of said third acid.

12. The sulfate-free surfactant system of claim 1 comprising 10-30 wt % said glyceride; 20-40 wt % said surfactant and 30-70 wt % water.

13. The sulfate-free surfactant system of claim 1 wherein said surfactant is selected from the group consisting of a cationic surfactant, an anionic surfactant, a nonionic surfactant and an amphoteric surfactant.

14. The sulfate-free surfactant system of claim 13 wherein said surfactant is selected from the group consisting of quaternized polysaccharides, alkyl polysaccharides, alkoxylated amines, alkoxylated ether amines, phospholipids, and mixtures thereof.

15. The sulfate-free surfactant system of claim 13 wherein said surfactant is selected from the group consisting of alkanoyl isethionates, alkyl succinates, alkyl sulphosuccinates, N-alkoyl sarcosinates, alkyl phosphates, alkyl ether phosphates, alkyl ether carboxylates, alpha-olefin sulphonates wherein alkyl and acyl groups are comprise 8 to 18 carbons and may be unsaturated.

16. The sulfate-free surfactant system of claim 13 wherein said surfactant is selected from the group consisting of sodium, magnesium, ammonium and mono-, di- and triethanolamine salts of alpha-olefin sulphonates.

17. The sulfate-free surfactant system of claim 13 wherein said surfactant is selected from the group consisting sodium oleyl succinate, ammonium lauryl sulphosuccinate, disodium laureth sulfosuccinate, sodium dodecylbenzene sulphonate, triethanolamine dodecylbenzene sulphonate, sodium cocoyl isethionate, sodium lauroyl isethionate, sodium N-lauryl sarconsinate, sodium lauroyl lactylate and sodium lauriminodipropionate.

18. The sulfate-free surfactant system of claim 17 wherein said surfactant is sodium lauriminodipropionate.

19. The sulfate-free surfactant system of claim 13 wherein said surfactant is selected from the group consisting of polyalkylene glycol adduct surfactants and glucoside surfactants either alone or as mixtures.

20. The sulfate-free surfactant system of claim 13 wherein said surfactant is selected from the group consisting of polyalkylene glycol adducts of alkyl C8-C24 phenols; polyalkylene glycol adducts of C8-C30 alcohols or C8-C30 glycosides, linear or branched, saturated or unsaturated; polyalkylene glycol adducts of C8-C30, linear or branched, saturated or unsaturated fatty acid amides; C8-C30 linear or branched, saturated or unsaturated esters of sorbitol, which are optionally polyalkylene glycol adducts; fatty acid esters of sucrose; C8-C30 alkyl polyglycosides; C8-C30 alkenyl polyglycosides, which are optionally polyalkylene glycol adducts with from 0 to 10 polyalkylene glycol units and comprising from 1 to 15 glucose units; polyalkylene glycol adducts of saturated or unsaturated vegetable oils; derivatives of N-alkyl (C8-C30) glucamine; derivatives of N-acyl C8-C30 methylglucamine; aldobionamides; amine oxides; polyalkylene glycol adducts of silicones; polyglycerin adducts of lauryl alcohol containing 1-7 moles of glycerin; polyglycerin adducts of oleyl alcohol containing 1-7 moles of glycerin; polyglycerin adducts of cetearyl alcohol containing 1-7 moles of glycerin; and polyglycerin adducts of octadecanol containing 1-7 moles of glycerin.

21. The sulfate-free surfactant system of claim 13 wherein said surfactant is selected from the group consisting of decyl glucoside, lauryl glucoside caprylic/capric glucoside and coco glucoside.

22. The sulfate-free surfactant system of claim 13 wherein said surfactant is selected from the group consisting of cocamidopropyl betaine, cocobetaine, sodium salt of diethylaminopropyl laurylaminosuccinamate or mixtures thereof.

23. The sulfate-free surfactant system of claim 1 wherein said surfactant is selected from the group consisting of disodium laureth sulfosuccinate, decyl glucoside sodium lauroyl lactylate and sodium lauriminodipropionate.

24. The sulfate-free surfactant system of claim 1 wherein said glyceride comprises the reaction product of glycerin with isostearic acid, octanoic acid and decanoic acid.

25. The sulfate-free surfactant system of claim 1 comprising less than 2 wt % sulphate-based surfactant.

26. The sulfate-free surfactant system of claim 25 comprising less than 1 wt % sulphate-based surfactant.

27. The sulfate-free surfactant system of claim 1 selected from the group consisting of a shampoo, a conditioner, a hand wash, a face wash, a body wash, a hand soothing liquid, an aromatic liquid, an eye care product, a cosmetic, a fragrance, a hair coloring formulation, a hair straightening or permanent wave formulation, a nail care formulation, a toothpaste, a mouthwash, a shave cream, a skin care formulation, a sun care formulation, a lip care formulation, an antiperspirant, or a foot care formulation.

28. A personal hygiene product comprising a sulfate-free surfactant system comprising:
   a liquid comprising an organic phase and a solvent wherein said organic phase comprises glyceride and surfactant and said liquid comprises:
   4-40 wt % glyceride wherein said glyceride is the condensation reaction product of at least 1.10 moles of a mixture of acids to no more than 2.1 moles of said mixture of acids per mole of glycerin;
   wherein said mixture of acids comprises:
   at least 0.275 to no more than 0.990 moles of a first acid comprising a branched acid with 16-20 aliphatic carbons;
   at least 0.250 to no more than 0.810 moles of a second acid comprising an alkyl acid with 9-11 carbons; and
   at least 0.250 to no more than 0.810 moles of a third acid comprising an alkyl acid with 7-9 carbons wherein said third acid has a lower molecular weight than said second acid; and
   6-45 wt % surfactant; and
   wherein said liquid has a BYV of at least 50 dyn/cm$^2$.

29. The personal hygiene product of claim 28 wherein said solvent is water.

30. The personal hygiene product of claim 29 comprising 10 to 95 wt % said organic phase and 10-90 wt % water.

31. The personal hygiene product of claim 28 wherein said BYV is at least 100 dyn/cm$^2$.

32. The personal hygiene product of claim 28 wherein said BYV does not exceed 100,000 dyn/cm$^2$.

33. The personal hygiene product of claim 28 wherein said mixture of acids comprises at least 0.425 moles of said second acid.

34. The personal hygiene product of claim 33 wherein said mixture of acids comprises at least 0.520 moles of said second acid.

35. The personal hygiene product of claim 28 wherein said mixture of acids comprises no more than 0.580 moles of said second acid.

36. The personal hygiene product of claim 28 wherein said mixture of acids comprises at least 0.425 moles of said third acid.

37. The personal hygiene product of claim 36 wherein said mixture of acids comprises at least 0.520 moles of said third acid.

38. The personal hygiene product of claim 28 wherein said mixture of acids comprises no more than 0.580 moles of said third acid.

39. The personal hygiene product of claim 28 comprising 10-30 wt % said glyceride; 20-40 wt % said surfactant and 30-70 wt % water.

40. The personal hygiene product of claim 28 wherein said surfactant is selected from the group consisting of a cationic surfactant, a anionic surfactant, a nonionic surfactant and an amphoteric surfactant.

41. The personal hygiene product of claim 40 wherein said surfactant is selected from the group consisting of quaternized polysaccharides, alkyl polysaccharides, alkoxylated amines, alkoxylated ether amines, phospholipids, and mixtures thereof.

42. The personal hygiene product of claim 40 wherein said surfactant is selected from the group consisting of alkanoyl isethionates, alkyl succinates, alkyl sulphosuccinates, N-alkoyl sarcosinates, alkyl phosphates, alkyl ether phosphates, alkyl ether carboxylates, alpha-olefin sulphonates wherein alkyl and acyl groups are comprise 8 to 18 carbons and may be unsaturated.

43. The personal hygiene product of claim 40 wherein said surfactant is selected from the group consisting of sodium, magnesium, ammonium and mono-, di- and triethanolamine salts of alpha-olefin sulphonates.

44. The personal hygiene product of claim 40 wherein said surfactant is selected from the group consisting of sodium oleyl succinate, ammonium lauryl sulphosuccinate, disodium laureth sulfosuccinate, sodium dodecylbenzene sulphonate, triethanolamine dodecylbenzene sulphonate, sodium cocoyl isethionate, sodium lauroyl isethionate, sodium N-lauryl sarconsinate, sodium lauroyl lactylate and sodium lauriminodipropionate.

45. The personal hygiene product of claim 44 wherein said surfactant is sodium lauriminodipropionate.

46. The personal hygiene product of claim 40 wherein said surfactant is selected from the group consisting of polyethylene glycol surfactants and glucoside surfactants either alone or as mixtures.

47. The personal hygiene product of claim 40 wherein said surfactant is selected from the group consisting of polyalkylene glycol adducts of alkyl C8-C24 phenols; polyalkylene glycol adducts of C8-C30 alcohols or C8-C30 glycosides, linear or branched, saturated or unsaturated; polyalkylene glycol adducts of C8-C30, linear or branched, saturated or unsaturated fatty acid amides; C8-C30 linear or branched, saturated or unsaturated esters of sorbitol, which are optionally polyalkylene glycol adducts; fatty acid esters of sucrose; C8-C30 alkyl polyglycosides; C8-C30 alkenyl polyglycosides, which are optionally polyalkylene glycol adducts with from 0 to 10 polyalkylene glycol units and comprising from 1 to 15 glucose units; polyalkylene glycol adducts of saturated or unsaturated vegetable oils; derivatives of N-alkyl (C8-C30) glucamine; derivatives of N-acyl C8-C30 methylglucamine; aldobionamides; amine oxides; polyalkylene glycol adducts of silicones; polyglycerin adducts of lauryl alcohol containing 1-7 moles of glycerin; polyglycerin adducts of oleyl alcohol containing 1-7 moles of glycerin; polyglycerin adducts of cetearyl alcohol containing 1-7 moles of glycerin; and polyglycerin adducts of octadecanol containing 1-7 moles of glycerin.

48. The personal hygiene product of claim 40 wherein said surfactant is selected from the group consisting of decyl glucoside, lauryl glucoside caprylic/capric glucoside and coco glucoside.

49. The personal hygiene product of claim 40 wherein said surfactant is selected from the group consisting of cocamidopropyl betaine, cocobetaine, sodium salt of diethylaminopropyl laurylaminosuccinamate or mixtures thereof.

50. The personal hygiene product of claim 28 wherein said surfactant is selected from the group consisting of disodium laureth sulfosuccinate, decyl glucoside sodium lauroyl lactylate and sodium lauriminodipropionate.

51. The personal hygiene product of claim 28 wherein said glyceride comprises the reaction product of glycerin with isostearic acid, octanoic acid and decanoic acid.

52. The personal hygiene product of claim 28 comprising less than 2 wt % sulfate-based surfactant.

53. The personal hygiene product of claim 52 comprising less than 1 wt % sulfate-based surfactant.

54. The personal hygiene product of claim 28 wherein said sulfate-free surfactant system is selected from the group consisting of a shampoo, a conditioner, a hand wash, a face wash, a body wash, a hand soothing liquid, an aromatic liquid, an eye care product, a cosmetic, a fragrance, a hair coloring formulation, a hair straightening or permanent wave formulation, a nail care formulation, a toothpaste, a mouthwash, a shave cream, a skin care formulation, a sun care formulation, a lip care formulation, an antiperspirant, or a foot care formulation.

* * * * *